United States Patent [19]

Takeshima

[11] Patent Number: 5,296,196
[45] Date of Patent: Mar. 22, 1994

[54] SEMICONDUCTOR HYDROCARBON SENSOR

[75] Inventor: Shinichi Takeshima, Susono, Japan

[73] Assignee: Toyota Jidosha Kabushiki Kaisha, Aichi, Japan

[21] Appl. No.: 823,720

[22] Filed: Jan. 22, 1992

[30] Foreign Application Priority Data

Feb. 4, 1991 [JP] Japan .................... 3-033365

[51] Int. Cl.$^5$ ............................ G01N 27/00
[52] U.S. Cl. ....................... 422/98; 422/94; 436/139; 436/152; 73/31.05; 73/31.06
[58] Field of Search ............... 422/94, 98; 436/139, 436/151, 152, 159; 73/31.05, 31.06

[56] References Cited

U.S. PATENT DOCUMENTS

| | | | |
|---|---|---|---|
| 3,631,436 | 12/1971 | Taguchi | 422/98 X |
| 4,016,524 | 4/1977 | Pompei et al. | 422/98 X |
| 4,111,658 | 9/1978 | Firth et al. | 422/98 X |
| 4,246,228 | 1/1981 | Jones et al. | 436/151 X |
| 4,259,292 | 3/1981 | Ichinose et al. | 422/98 |
| 4,294,801 | 10/1981 | Segawa et al. | 422/98 |
| 4,347,732 | 9/1982 | Leary | 73/31.05 |
| 4,453,151 | 6/1984 | Leary et al. | 422/98 X |
| 4,944,273 | 7/1990 | Baresel et al. | 73/31.06 X |
| 5,017,538 | 5/1991 | Takeshima | 502/60 X |
| 5,143,696 | 9/1992 | Haas et al. | 422/98 X |

FOREIGN PATENT DOCUMENTS 3519435 12/1986 Fed. Rep. of Germany.
359450 7/1989 Japan.

OTHER PUBLICATIONS

The Merck Index, 1983, p. 52.

Primary Examiner—James C. Housel
Assistant Examiner—Maureen M. Wallenhorst
Attorney, Agent, or Firm—Kenyon & Kenyon

[57] ABSTRACT

A semiconductor-type hydrocarbon sensor includes an oxide semiconductor, an outer electrode formed on an outside surface of the oxide semiconductor, an inner electrode formed on an inside surface of the oxide semiconductor, and a zeolite layer constructed of zeolite carrying at least one metal selected from the group consisting of platinum and copper. Small molecular weight hydrocarbons enter pores of the zeolite layer and are oxidized so that the small molecular weight hydrocarbons cannot reach the oxide semiconductor. Large molecular weight hydrocarbons cannot enter the small pores of the zeolite layer and, instead, pass through grain boundaries of zeolite particles of the zeolite layer to reach the oxide semiconductor. As a result, the large molecular weight hydrocarbons are selectively detected by the semiconductor-type hydrocarbon sensor.

10 Claims, 1 Drawing Sheet

SEMICONDUCTOR HYDROCARBON SENSOR

BACKGROUND OF THE INVENTION

1. Field of the Invention

The present invention relates to a semiconductor-type hydrocarbon sensor which can selectively detect large molecular weight hydrocarbons (HC).

2. Description of the Prior Art

Lean burn engines, which are defined as engines conducting fuel combustion at lean air-fuel ratios, are known for improving fuel economy and suppressing exhaust of carbon dioxide. Since nitrogen oxides (NOx) cannot be reduced by a three-way catalyst in the lean burn engines, a zeolite catalyst which can reduce NOx even under oxidizing conditions (lean air-fuel ratio conditions) has been developed.

The zeolite catalyst needs hydrocarbons to reduce NOx. Further, the NOx purification rate of the zeolite catalyst is affected by not only the amount of hydrocarbons to be supplied but also the kinds of the hydrocarbons. More particularly, the NOx purification rate of the zeolite catalyst is affected by whether the hydrocarbon molecular weight is large (for example, the number of carbon atoms included in the HC molecule is equal to or greater than six) or small (for example, the number of carbon atoms included in the HC molecule is equal to or smaller than five). For example, methane, which has only one carbon atom in each molecule, has little effect in purifying NOx. Further, the relatively small molecular weight hydrocarbons are effective in purifying NOx at relatively low temperatures, and the relatively large molecular weight hydrocarbons are effective in purifying NOx at relatively high temperatures.

To use the zeolite catalyst effectively in an exhaust conduit of a lean burn engine to purify NOx, it is necessary to install a hydrocabon sensor for detecting the amount of HC included in the exhaust gas and to feed back the output of the sensor to control the amount of HC included in the exhaust gas.

As an example of such hydrocarbon sensors, a semiconductor-type hydrocarbon sensor is known from the publication: "Chemical Sensors" edited by Tetsurou Mizoyama and published by Koudansha on Mar. 1, 1982. The prior art semiconductor-type hydrocarbon sensor includes an insulation base, paired electrodes, and a metal oxide (oxide semiconductor) provided between the paired electrodes. In such a sensor, the HC concentration of the exhaust gas is detected by measuring a change in the electrical resistance of the oxide semiconductor.

However, the prior art semiconductor-type hydrocarbon sensor detects only the total amount of hydrocarbons and cannot detect the kinds of the hydrocarbons. As discussed above, since NOx purification by the zeolite catalyst is affected by not only the amount of hydrocarbons but also the kinds of the hydrocarbons, it is desirable to develop a semiconductor-type hydrocarbon sensor capable of also determining the kinds of hydrocarbons.

Further, there is a close relationship between combustion of an engine and the kinds of hydrocarbons included in the exhaust gas from the engine. For example, when the combustion is slow, the amount of large molecular weight hydrocarbons (for example, toluene, iso-octane) increases. This phenomenon is strongly seen at low engine speeds and when exhaust gas recirculation (EGR) is being conducted. Therefore, if a semiconductor-type hydrocarbon sensor capable of detecting even the kinds of hydrocarbons can be developed, such a sensor can be used for controlling conventional engines, too.

SUMMARY OF THE INVENTION

An object of the invention is to provide a semiconductor-type hydrocarbon sensor which can selectively detect large molecular weight hydrocarbons for use in NOx purification control of lean burn engines and for combustion control of conventional engines.

The above-described object can be attained by a semiconductor-type hydrocarbon sensor in accordance with the present invention. The sensor includes an oxide semiconductor, an outer electrode provided on at least a portion of an outside surface of the oxide semiconductor, an inner electrode provided at an inside surface of the oxide semiconductor, and a zeolite layer carrying at least one metal selected from the group consisting of noble metals, transition metals, and alkaline-earth metals provided at the outside surface of the oxide semiconductor so as to cover the portion of the outside surface of the oxide semiconductor where the outer electrode is provided.

In the semiconductor-type hydrocarbon sensor of the present invention, since the zeolite layer carrying the at least one metal selected from the group consisting of noble metals, transition metals, and alkaline-earth metals is formed at the outside surface of the oxide semiconductor, small molecular weight hydrocarbons that enter the small pores of the zeolite layer are oxidized into water and carbon dioxide and cannot reach the detecting portion formed by the oxide semiconductor. In contrast, since the sizes of large molecular weight hydrocarbons are larger than the sizes of the pores of the zeolite layer, these large hydrocarbons cannot enter the pores of the zeolite layer. Instead, the large molecular weight hydrocarbons pass through the grain boundaries of the zeolite particles to reach the oxide semiconductor, where they react with oxygen atoms of the oxide semiconductor freeing the electrons of the oxygen atoms to increase the conductivity of the n-type semiconductor. The increased conductivity is detected by the paired inner and outer electrodes, so that the amount of the large molecular weight hydrocarbons is selectively measured.

BRIEF DESCRIPTION OF THE DRAWINGS

The above and other objects, features, and advantages of the present invention will become more apparent and will be more readily appreciated from the following detailed description of the preferred embodiments of the invention taken in conjunction with the accompanying drawings, in which.

DETAILED DESCRIPTION OF THE PREFERRED EMBODIMENTS

Figure 1:
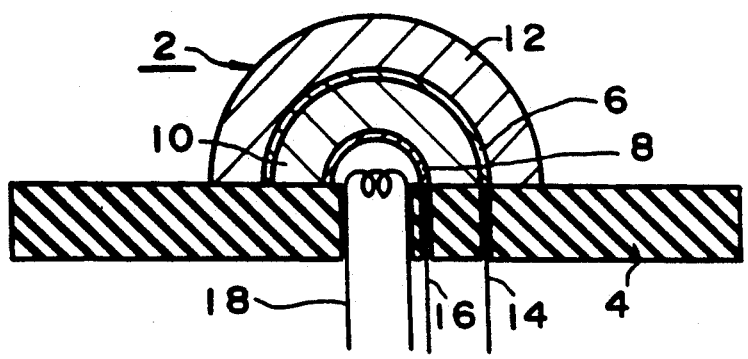
FIG. 1 is a cross-sectional view of a semiconductor-type hydrocarbon sensor in accordance with a first embodiment of the present invention.
Figure 2:
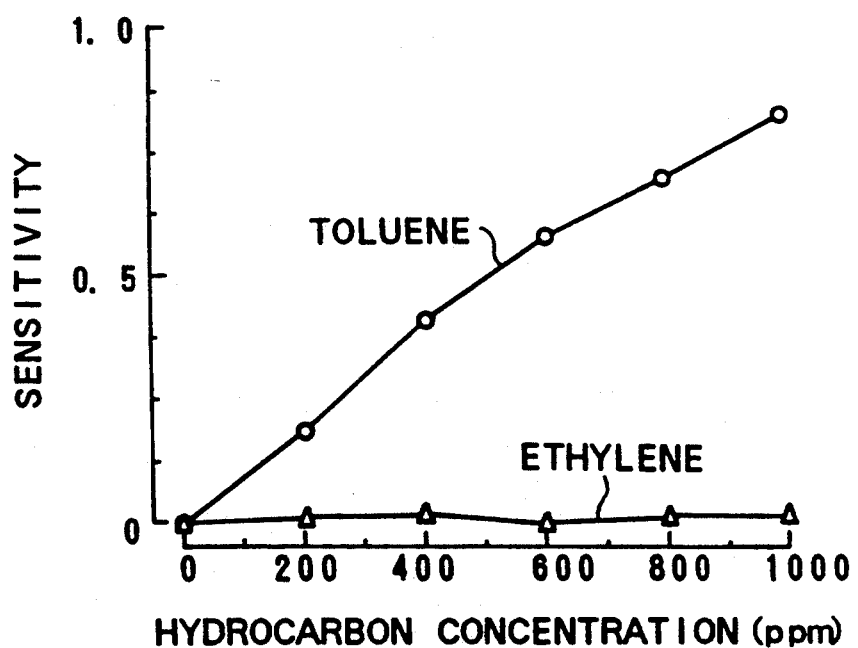
FIG. 2 is a graphical representation of equi-carbon relative sensitivity versus hydrocarbon concentration characteristic of toluene (a typical large molecular weight hydrocarbon) and ethylene (a typical small molecular weight hydrocarbon) obtained from a test conducted using the hydrocarbon sensor of FIG. 1.

As illustrated in FIG. 1, a semiconductor-type hydrocarbon sensor in accordance with a first embodiment of the present invention includes an insulation base 4, an oxide semiconductor 10 supported by the insulation base 4, an outer electrode 6 provided on an outside surface of the oxide semiconductor 10, an inner electrode 8 provided on an inside surface of the oxide semiconductor 10, a zeolite layer 12 constructed of zeolite carrying at least one metal selected from the group consisting of noble metals, transition metals, and alkaline-earth metals through ion exchange and provided on at least a portion of the outside surface of the oxide semiconductor 10 so as to cover the outer electrode 6, and a heater 18 disposed inside the oxide semiconductor 10.

The insulation base 4 is a flat plate, and the oxide semiconductor 10 and the zeolite layer 12 are semispherical. The insulation base 4 is constructed of heat-resistant, electrically insulating material, for example, alumina. The electrodes 6 and 8 are paired to each other and are constructed of platinum wire. The electrodes 6 and 8 are connected to signal transmitting wires 14 and 16, respectively.

The oxide semiconductor 10 is constructed of an n-type semiconductor such as tin oxide ($SnO_2$) The zeolite of the zeolite layer 12 has many pores with small sizes (4–6 angstroms) for selectively catching small molecular weight hydrocarbons. In this instance, if the pores size were smaller than 4 angstroms, the small molecular weight hydrocarbons would not be caught by the cells, and if the pore size were larger than 6 angstroms, even the large molecular weight hydrocarbons would be caught in the pore to be oxidized therein. ZSM-5, offretite, erionite, and ferrierite are included in such zeolite having small pores. The noble metals carried by the zeolite include platinum (Pt), and the transition metals carried by the zeolite include copper (Cu). The catalyst metals oxidize the hydrocarbons caught in the pores into water and carbon dioxide. A thickness of the catalyst metal carried by the zeolite is in the range of 50–100 microns. The 50–100 micron range of the catalyst metal is selected to obtain both electric conductivity and porosity.

To effectively measure the hydrocarbon concentration of the exhaust gas exhausted from a lean burn engine using the semiconductor-type hydrocarbon sensor 2 in accordance with the first embodiment, the hydrocarbon sensor 2 should be installed at a portion of an exhaust conduit of the engine with an exhaust gas temperature 350° C.–400° C. and should be mounted in the exhaust conduit so that the zeolite layer side is exposed to the exhaust gas. The reason why the sensor is used in the temperature range 350° C.–400° C. is that the electric resistance of the $SnO_2$ semiconductor is in an appropriate range from the viewpoint of measurement and the response of the semiconductor is high in that temperature range.

Hydrocarbons included in the engine exhaust gas include various molecular weight hydrocarbons, for example, small molecular weight hydrocarbons (the number of carbon atoms included in a molecule is equal to or less than 5, and ethylene, propylene, and iso-pentane are included in the small molecular weight hydrocarbons) and large molecular weight hydrocarbons (the number of carbon atoms included in a molecule is equal to or greater than 6). The small molecular weight hydrocarbons enter the small pores of the zeolite where the hydrocarbons are oxidized into water and carbon dioxide. Therefore, the small molecular weight hydrocarbons cannot reach the oxide semiconductor 10. In contrast, the large molecular weight hydrocarbons cannot enter the small pores of the zeolite because the sizes of the hydrocarbons are larger than the pore sizes. The large molecular weight hydrocarbons pass through the grain boundaries between the zeolite particles to reach the oxide semiconductor 10. The large hydrocarbons having reached the oxide semiconductor 10 react with oxygen atoms of the oxide semiconductor 10 so that electrons of the oxygen atoms are freed and the conductivity of the n-type semiconductor 10 is increased. The increase in the conductivity is detected by measuring a change in electric current flowing between the paired electrodes 6 and 8 so that the amount of large molecular weight hydrocarbons is selectively measured.

The reason why the sensor should be installed at the exhaust gas conduit portion with the gas temperature 350° C.–400° C. is as follows: If the exhaust gas temperature at the sensor mounting portion were lower than 350° C., the zeolite itself would be inactive, and if the exhaust gas temperature at the sensor mounting portion were higher than 400° C., the large molecular weight hydrocarbons would be decomposed to smaller molecular weight hydrocarbons which would be caught in the zeolite pore and oxidized.

Figure 3:
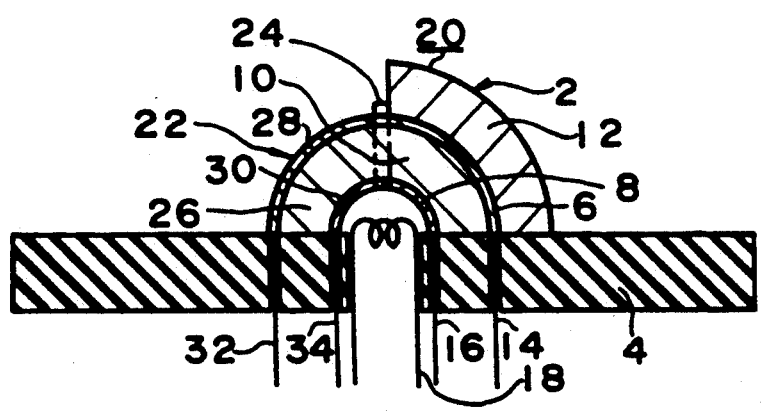
FIG. 3 is a cross-sectional view of a semiconductor-type hydrocarbon sensor in accordance with a second embodiment of the present invention.

FIG. 3 illustrates a semiconductor-type hydrocarbon sensor 20 in accordance with a second embodiment of the present invention. In FIG. 3, the portions of the sensor in accordance with the second embodiment having structures similar to those of the sensor in accordance with the first embodiment are denoted with the same reference numerals as those of the first embodiment. As shown in FIG. 3, the hydrocarbon sensor of the second embodiment includes a first sensor portion 2 for selectively detecting large molecular weight hydrocarbons like the hydrocarbon sensor of the first embodiment and a second sensor portion 22, separated from the first sensor portion 2 by a gas barrier 24, and capable of detecting all kinds of hydrocarbons like the conventional hydrocarbon sensors.

The first sensor portion 2 includes an insulation base 4, an oxide semiconductor 10 supporting the insulation base 4, an outer electrode 6 provided on an outside surface of the oxide semiconductor 10, an inner electrode 8 provided on an inside surface of the oxide semiconductor 10, a zeolite layer 12 provided on at least a portion of the outside surface of the oxide semiconductor 10 so as to cover the outer electrode 6, and a heater 18 provided inside the oxide semiconductor 10. The zeolite layer 12 includes zeolite having small pores with sizes of 4–6 angstroms and carrying at least one metal selected from the group consisting of noble metals, transition metals, and alkaline-earth metals by ion exchange.

The second sensor portion 22 includes an insulation base 4 which is integral with the insulation base 4 of the first sensor portion 2, an oxide semiconductor 26 which is integral with the oxide semiconductor 10 of the first sensor portion 2 though there is no gas flow between the two oxide semiconductors 10 and 26 because of the gas barrier layer 24 provided between the two oxide semiconductors 10 and 26, an outer electrode 28 provided on an outside surface of the oxide semiconductor 26, an inner electrode 30 provided on an inside surface of the oxide semiconductor 26, and a heater 18 which is provided inside the oxide semiconductor 26 and is common with the heater 18 of the first sensor portion 2. The electrodes 28 and 30 are connected to signal transmitting wires 32 and 34, respectively. The outer electrode 28 of the second sensor portion 22 and the outer electrode 6 of the first sensor portion 2 are insulated from each other, and the inner electrode 30 of the second sensor portion 22 and the inner electrode 8 of the first sensor portion 2 are insulated from each other.

Measuring the amount of hydrocarbons included in exhaust gas from a lean burn engine using the hydrocarbon sensor of the second embodiment, the electrodes 6 and 8 of the first sensor portion 2 selectively detect the large molecular weight hydrocarbons and the electrodes 28 and 30 of the second sensor portion 22 detect both small and large molecular weight hydrocarbons. More particularly, since the zeolite layer 12 is provided on the first sensor portion 2, the small molecular weight hydrocarbons are oxidized in the zeolite layer 12 and cannot reach the oxide semiconductor 10. In contrast, since there is no zeolite layer on the second sensor portion 22, both small and large molecular weight hydrocarbons can reach and contact the oxide semiconductor 26.

By subtracting the amount of large molecular weight hydrocarbons detected by the first sensor portion 2 from the amount of all kinds of hydrocarbons detected by the second sensor portion 22, the amount of small molecular weight hydrocarbons in the exhaust gas is obtained.

The above-described hydrocarbon sensors in accordance with the first and second embodiments can be used not only for hydorcarbon control for NOx reduction control of a lean burn engines but also for hydrocarbon decrease control for a conventional engine.

In accordance with the present invention, since the zeolite layer catalyst carrying at least one metal selected from the group consisting of platinum and copper is provided on the outside surface of the oxide semiconductor, the small molecular weight hydrocarbons are prevented from reaching the oxide semiconductor, so that the large molecular weight hydrocarbons can be selectively detected.

Though a few embodiments of the present invention have been described in detail above, it will be appreciated by those skilled in the art that various modifications and alterations can be made to the particular embodiments shown without materially departing from the novel teachings and advantages of the present invention. Accordingly, it is to be understood that all such modifications and alterations are included within the spirit and scope of the present invention as defined by the following claims.

What is claimed is:

1. A semiconductor hydrocarbon sensor comprising:
   an oxide semiconductor having an outside surface and an inside surface;
   an outer electrode provided on at least a portion of the outside surface of the oxide semiconductor;
   an inner electrode provided on at least a portion of the inside surface of the oxide semiconductor; and
   a zeolite layer constructed of a porous zeolite carrying at least one metal selected from the group consisting of platinum and copper formed discretely from said oxide semiconductor and provided on the portion of the outside semiconductor and provided on the portion of the outside surface of the oxide semiconductor on which the outer electrode is provided so as to cover the outer electrode, wherein small molecular weight hydrocarbons having five or less carbon atoms enter the pores of the zeolite and are oxidized by the metal carried therein so that the small molecular weight hydrocarbons are substantially absorbed in the zeolite layer before reaching the oxide semiconductor and large molecular weight hydrocarbons having six or more carbon atoms pass through paths formed between the grain boundaries of the zeolite layer to reach the oxide semiconductor.

2. A semiconductor hydrocarbon sensor according to claim 1 and further comprising:
   an insulation base supporting the oxide semiconductor; and
   a heater disposed inside the oxide semiconductor.

3. A semiconductor hydrocarbon sensor according to claim 2, wherein the insulation base is a flat plate, and the oxide semiconductor and the zeolite layer are semispherical.

4. A semiconductor hydrocarbon sensor according to claim 2, wherein the insulation base is constructed of alumina, and the inner electrode and the outer electrode are paired to each other and are constructed of platinum wire.

5. A semiconductor hydrocarbon sensor according to claim 1, wherein the pores of the zeolite constituting the zeolite layer have sizes of 4-6

6. A semiconductor hydrocarbon sensor according to claim1, wherein the metal selected from the group consisting of platinum and copper carried by the zeolite has a thickness of 50-100 microns.

7. A semiconductor hydrocarbon sensor comprising:
   a first sensor portion for selectively detecting large molecular weight hydrocarbons having six or more carbon atoms; and
   a second sensor portion, separated from the first sensor portion by a gas barrier layer, for detecting small molecular weight hydrocarbons having five or less carbon atoms and said large molecular weight hydrocarbons.

8. A semiconductor hydrocarbon sensor according to claim 7, wherein the first sensor portion comprises:
   an oxide semiconductor having an outside surface and an inside surface;
   an outer electrode provided on at least a portion of the outside surface of the oxide semiconductor;
   an inner electrode provided on at least a portion of the inside surface of the oxide semiconductor;
   a zeolite layer constructed of a porous zeolite carrying at least one metal selected from the group consisting of platinum and copper and provided on the portion of the outside surface of the oxide semiconductor on which the outer electrode is provided so as to cover the outer electrode;
   an insulation base supporting the oxide semiconductor; and
   a heater disposed inside the oxide semiconductor.

9. A semiconductor hydrocarbon sensor according to claim 8, wherein the pores of the zeolite constituting the zeolite layer have sizes of 4-6 angstroms.

10. A semiconductor hydrocarbon sensor according to claim 8, wherein the second sensor portion comprises:
    a second insulation base which is integral with the insulation base of the first sensor portion;

a second oxide semiconductor which is coupled to the oxide semiconductor of the first sensor portion so that the gas barrier layer is positioned between the oxide semiconductor of the first sensor portion and the oxide semiconductor of the second sensor portion;

a second outer electrode provided on an outside surface of the oxide semiconductor of the second sensor portion and electrically insulated from the outer electrode of the first sensor portion; and a second inner electrode provided on an inside surface of the oxide semiconductor of the second sensor portion and electrically insulated from the inner electrode of the first sensor portion.

* * * * *

UNITED STATES PATENT AND TRADEMARK OFFICE
CERTIFICATE OF CORRECTION

PATENT NO. : 5,296,196
DATED : March 22, 1994
INVENTOR(S) : Shinichi Takeshima

It is certified that error appears in the above-indentified patent and that said Letters Patent is hereby corrected as shown below:

Column 6, line 30, after "4-6" insert --angstroms.--
line 32, change "claiml" to --claim 1--.

Signed and Sealed this

Fourth Day of October, 1994

Attest:

BRUCE LEHMAN

*Attesting Officer*     *Commissioner of Patents and Trademarks*